United States Patent
Mollette et al.

[11] Patent Number: 6,163,902
[45] Date of Patent: Dec. 26, 2000

[54] TRAUMA TABLE TOP

[76] Inventors: Julie M. Mollette, 1717 Carlsbad Dr., Lafayette, Ind. 47905; Brenda Ann Denney, 5994 N. US Hwy 45, Watson, Ill. 62473

[21] Appl. No.: 09/387,177

[22] Filed: Oct. 22, 1999

[51] Int. Cl.[7] .................................................. A61B 6/00
[52] U.S. Cl. .............................. 5/601; 378/177; 378/209
[58] Field of Search ................................ 5/600, 601, 694; 378/209, 177

[56] References Cited

U.S. PATENT DOCUMENTS

| | | | |
|---|---|---|---|
| 1,241,136 | 9/1917 | Meyer | 378/179 |
| 1,980,848 | 11/1934 | Cass | 5/601 X |
| 2,989,634 | 6/1961 | Ould et al. | 378/177 |
| 3,065,344 | 11/1962 | Chervenka | 378/177 |
| 3,215,834 | 11/1965 | Tayman | 5/601 X |
| 3,411,766 | 11/1968 | Lanigan | 378/177 X |
| 3,648,305 | 3/1972 | Ersek | 5/601 X |
| 3,763,375 | 10/1973 | Scheninger | 378/177 |
| 3,774,045 | 11/1973 | Trott | 378/177 X |
| 3,904,531 | 9/1975 | Barrett et al. | 378/177 X |
| 3,967,126 | 6/1976 | Otto, Jr. | 378/177 |
| 3,967,128 | 6/1976 | Smulewicz | 5/601 X |
| 3,997,792 | 12/1976 | Conrad et al. | 378/177 |
| 4,038,709 | 8/1977 | Kerwit | 5/601 |
| 4,067,565 | 1/1978 | Daniels | 5/601 |
| 4,071,767 | 1/1978 | Pury et al. | 378/177 X |
| 4,103,170 | 7/1978 | Spradlin | 5/601 X |
| 4,193,148 | 3/1980 | Rush | 5/601 X |
| 4,205,233 | 5/1980 | Craig et al. | 378/209 X |
| 4,417,357 | 11/1983 | Le Sonn | 378/177 |
| 4,559,641 | 12/1985 | Cougant et al. | 378/209 X |
| 4,584,989 | 4/1986 | Stith | 5/601 X |
| 4,635,914 | 1/1987 | Kabanek | 5/601 X |
| 4,651,364 | 3/1987 | Hayton et al. | 5/601 |
| 4,669,136 | 6/1987 | Waters et al. | 5/601 |
| 4,873,710 | 10/1989 | Lotman | 5/601 X |
| 4,893,323 | 1/1990 | Cook, III . | |
| 4,916,725 | 4/1990 | Quinter et al. | 5/601 X |
| 4,947,418 | 8/1990 | Barr et al. . | |
| 4,995,067 | 2/1991 | Royster et al. | 5/601 X |
| 5,016,268 | 5/1991 | Lotman | 5/601 X |
| 5,166,968 | 11/1992 | Morse . | |
| 5,190,056 | 3/1993 | Hull . | |
| 5,243,639 | 9/1993 | Johnson . | |
| 5,255,303 | 10/1993 | DiMaio et al. . | |
| 5,422,928 | 6/1995 | Payne . | |
| 5,473,784 | 12/1995 | Nixon et al. . | |
| 5,703,925 | 12/1997 | Wright | 378/177 X |
| 5,996,149 | 12/1999 | Heimbrock et al. | 5/601 |

*Primary Examiner*—Terry Lee Melius
*Assistant Examiner*—Robert G. Santos
*Attorney, Agent, or Firm*—Michael Berns; Berns Law Office

[57] ABSTRACT

An x-ray trauma board having a rigid, flat, radiolucent, substantially transparent top support separated from a flat, rigid base by a plurality of spacers along either side of the board, leaving spaces along either side of the board through which an x-ray cassette may be inserted. The top support, base, and spacers define an open space in which the cassette may be positioned. The top support is hinged to the spacers along one side of the board for raising and lowering of the top support.

19 Claims, 3 Drawing Sheets

TRAUMA TABLE TOP

BACKGROUND OF THE INVENTION

This invention relates generally to the field of medical trauma boards and, more particularly, to an improved x-ray trauma board for supporting a patient while allowing x-ray diagnosis of the patient.

X-ray examinations are typically a first step in the treatment of trauma victims. It is well known to those in the medical profession that emergency room patients are often moved from a board to an x-ray table for x-ray examination, including examination of the head, chest, abdominal, or other areas. Typically, the patient then is moved to another trauma table for the next step in treatment. Even if the patient is not transferred from table to table, the patient may need to be manipulated in ways such as lifting, bending, or positioning, for placement of an x-ray cassette during x-ray examination. When the x-ray cassette is placed underneath of the patient for examination, the patient must be moved. These repeated movements of the patient can be harmful or fatal for some trauma victims. Additional x-ray examinations may need to be performed, compounding the problem. There is a need in the art for an x-ray trauma table that can be used to support a patient with minimal patient movement during various stages of treatment, including x-ray diagnosis.

Prior art devices have attempted to meet this need, but none have all of the advantages of the present invention. U.S. Pat. No. 4,947,418 to Barr et al. discloses a rather complex "emergency trauma board" which allows the placement of an x-ray cartridge in specific channels between an upper metal frame holding a rigid, translucent panel therein and a lower metal frame holding a fluid permeable panel. While a plurality of channels are provided for insertion of an x-ray cartridge, the positions available are finite and specific, eliminating flexibility and ease as to the placement of a cartridge. U.S. Pat. No. 4,893,323 to Cook, III discloses a "combination portable x-ray table and stretcher" containing an upper support and lower support spaced apart by a pair of side supports extending fully along the sides of the table. Cartridges may be inserted only via distantly opposed end channels, and positioning of a cartridge requires cumbersome and imprecise use of a "push stick" at the ends of the table while looking through the sides of the table for guidance. In addition, the table must be raised as a whole, making the table difficult to clean. U.S. Pat. No. 5,255,203 to DiMaio et al. discloses an "multi-purpose emergency room trauma board" containing a base with an elevated lip around the perimeter, a separate, removable board, and support means for separating the base and the board to allow insertion and positioning of an x-ray cassette between the base and board. While this board allows more flexibility of cassette positioning, the top board can easily slide and move laterally on top of the spacers, even becoming accidentally disengaged from one or more of the support means, possibly resulting in the patient movement that is sought to be prevented. In addition, the patient is not supported on this board as well as he/she would be on the present invention.

There is a need in the art for an x-ray trauma board which allows the patient to be placed onto the board and fully supported while x-ray cassettes are easily placed into any desired position for diagnosis without having to move the patient, and without risk that the patient will accidentally be moved along with the top of the board. There is a further need in the art for an x-ray trauma board that is simple and economical to construct, and one that may be cleaned and maintained after use.

BRIEF SUMMARY OF THE INVENTION

The object of the present invention is to provide a portable table for transporting the patient on which the patient can also be x-rayed without any unnecessary movement.

A further object of the invention is to provide such a table with a transparent surface and open sides such that an x-ray cartridge may be easily positioned beneath the patient in the most appropriate place to obtain the best result for the most efficient diagnosis.

An additional object of the invention is to provide such a table that may be easily and efficiently cleaned when not in use. This is accomplished by the hinges which allow for the top support to be opened and swung away from the bottom support for easy cleaning.

The invention is a portable x-ray trauma table that can be used immediately upon arrival at the hospital for necessary x-rays and other medical procedures. An ambulance backboard or other patient carrying support can be placed directly on the invention. Thus, the only movement of the patient that is necessary is the initial placement of the patient on the table. The table is rigid to allow the performance of CPR and other life-saving techniques and it has a transparent top and open sides for the exact placement of x-ray cartridges to more efficiently diagnose the patient's medical needs.

These needs and others are met by the present invention, an x-ray trauma board which is comprised of a flat, rigid base, a flat, rigid, radiolucent, substantially transparent top support for supporting a patient in an immobilized position, and a plurality of spacers mounted to the top surface of the base along both opposing sides of the base. The plurality of spacers on each side provide support for the top support, and the spacers on one side are hinged to the top support for securing the top support, while still allowing the top support to be raised for cleaning or for other purposes. The spacers are separated along each side, and at least one opening is left along the sides for insertion of an x-ray cassette. The top support, base, and spacers define an open space from end to end, side spacer to side spacer, and from base to top support for flexible positioning of the cassette, while the patient remains immobilized on the top support. The transparency of the complete top support provides for ease and precision in cassette positioning. The side of the top support opposite from the hinged side may be latched to the spacers for further stability. For increased support, spacers may be mounted to the ends of the base, extending along each end. Preferably, the invention employs spacers having a rectangular cross-section, such as blocks. If desired, the head end of the trauma board may be indented along either side for better access to the head of the patient, as well as improved positioning of an x-ray cassette for head x-rays. The present invention is simple to construct and maintain, and it provides maximum support for the patient and maximum flexibility, precision, and ease of x-ray cassette insertion and positioning, while minimizing movement, intentional or accidental, of the patient.

It is an object of the invention to provide an x-ray trauma board that supports a patient safely while allowing easy, flexible and exact positioning of an x-ray cassette, and without requiring movement of the patient.

Other objects, advantages, and novel features of the invention will become apparent from the following detailed description and appended claims, when taken in conjunction with the accompanying drawings.

Figure 1:
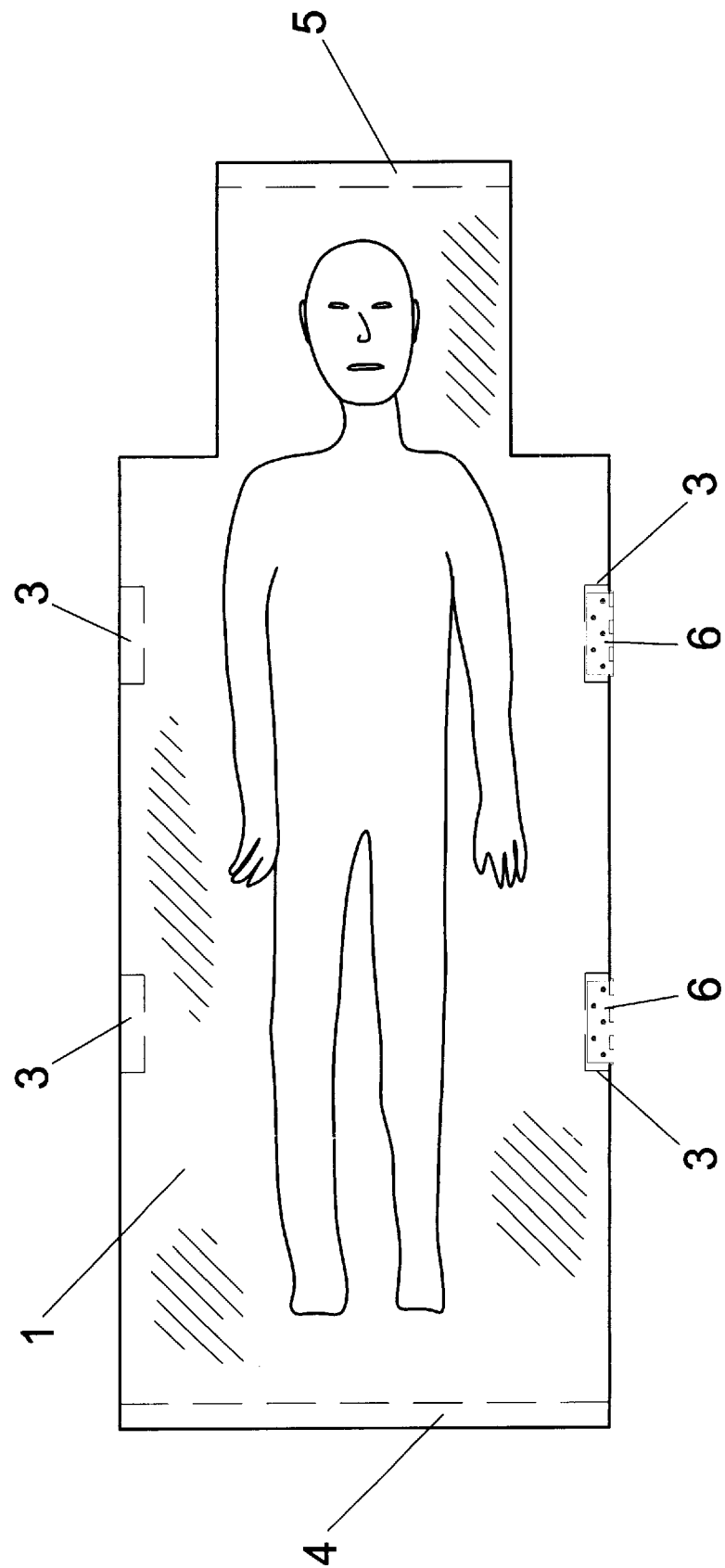
FIG. 1 shows a top plan view of an embodiment of the invention.

REFERENCE NUMERALS USED IN THE DRAWINGS 1 top support
2 base
3 side spacers
4 spacer at foot of table
5 spacer at head of table
6 hinges

DETAILED DESCRIPTION OF THE PREFERRED EMBODIMENT

Referring to FIG. 1, a top plan view of an embodiment of the present invention, an x-ray trauma board, is shown. A patient (shown but not numbered) is able to lay on an upper surface of a flat, rigid top support 1, the top support 1 being both radiolucent; i.e., easily penetrable by x-rays, and substantially transparent. The rigidity of the board allows the performance of CPR and other life-saving techniques on the top support. In a preferred embodiment, the top support is constructed of a transparent acrylic plastic, such as PLEXIGLAS, or LEXAN. Preferably, the top support 1 is approximately two feet wide and six feet long. In use, the head end of the top support would be used to support the head of the patient. Because the top support 1 is easily penetrable by x-rays, an x-ray technician is able to place x-ray cassettes underneath the top support 1, and onto the upper surface of a rigid base 2 underneath of the top support 1, for effective x-ray analysis of the patient without having to move the patient. This advantage of the invention is especially helpful for technicians dealing with patients in serious trauma situations, where it may be severely harmful, or even fatal, to move the patient once the patient is situated on the trauma board, or to transfer the patient from the board, before proper care can be administered. Preferably, the top support 1 and base 2 are each about one inch thick for sufficient rigidity and support.

Figure 2:
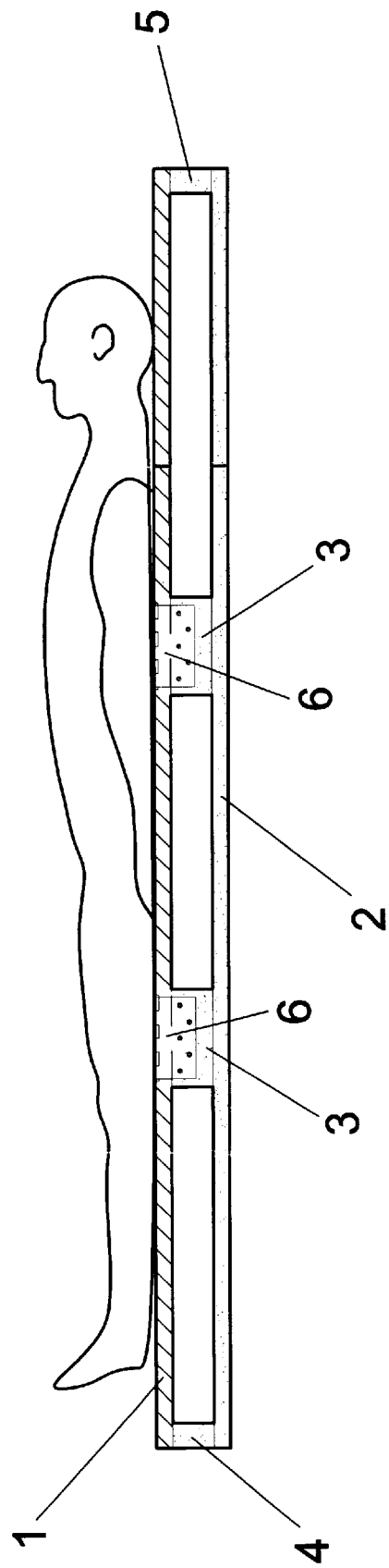
FIG. 2 shows a side elevation view of an embodiment of the invention.

FIG. 2 shows a side elevation view of an embodiment of the invention. The top support 1 rests on a plurality of side spacers 3 which serve to vertically separate the top support 1 from the rigid base 2 in a parallel relationship, the rigid base 2 being configured to rest upon a table, bed, gurney, floor, or other location for treatment of the patient. The spacers may be made of an electrically non-conductive material, such as wood or plastic, to allow electrical isolation of the invention. Preferably, the base 2 has the same length and width as the top support 1, two feet wide by six feet long. The base is constructed of a rigid material. The base also has an upper surface, a lower surface, and a head end and foot end corresponding to the ends of the top support 1.

Figure 3:
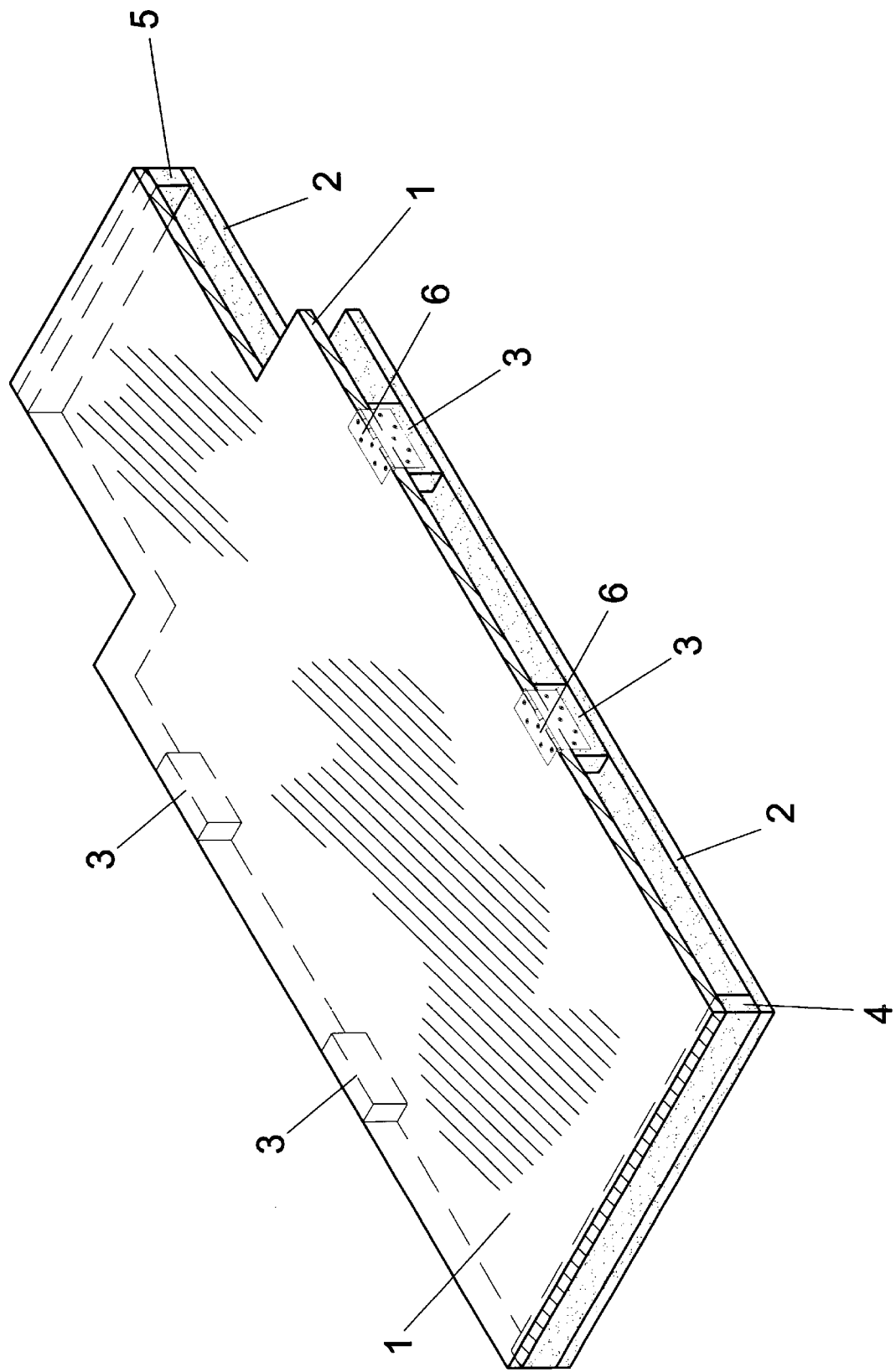
FIG. 3 shows a perspective view of an embodiment of the invention.

The side spacers 3 are mounted to the base 2 and extend axially along each opposing side of the base 2, as shown most clearly in FIG. 3, a perspective view of an embodiment of the invention. There are at least two side spacers 3 mounted to each of the two opposed sides of the base 2, preferably along the periphery of each side. The side spacers 3 preferably each have a rectangular cross-section, and optimally the side spacers comprise rectangular blocks. The use of blocks as side spacers, and the plurality of side spacers on each side, are advantageous over the prior art because there is an increased upper spacer surface area in contact with the lower surface of the top support 1. This provides increased support for the top support 1 and the patient stationed upon the top support, particularly when the blocks are evenly spaced along each side of the base 2. The side spacers may be placed directly across from one another on opposing sides, as shown most clearly in FIG. 1. Preferably, a foot end spacer 4 and a head end spacer 5 are also mounted to the base 2, running along the entire periphery of each end, as shown most clearly in FIG. 1. The side spacers 3, head end spacer 5, and foot end spacer 4 have a height sufficient to allow the insertion of an x-ray cassette (not shown) between the top support 1 and the base 2. Preferably, for standard x-ray cassettes, this height is approximately two inches in height. The side spacers 3 must be placed along the sides of the trauma board so as to leave at least one opening along either or both sides of the trauma board for insertion of the x-ray cartridge. Preferably, openings are left along both sides of the trauma board for easy insertion of the x-ray cartridge. FIG. 2 shows a placement of side spacers 3 that serves to leave three such openings along one side of the x-ray trauma board. The left and right openings are created from the separation of a side spacer 3 from the foot end spacer 4 and the head end spacer 5, respectively. The middle opening is created from the separation of the two side spacers 3. The use of openings along the sides of the trauma board is advantageous for easy insertion and positioning of the x-ray cassette, versus openings solely along the ends as in some prior art.

The end spacers 4, 5, the side spacers 3, the top support 1, and the base 2 serve to define an open space for positioning of the x-ray cassette anywhere within the open space after insertion. The open space has a length extending from the head end 5 to the foot end 4 of the trauma board, a width extending from the side spacers 3 on one side to the side spacers 3 on the opposite side, and a height extending from the upper surface of the base 2 to the lower surface of the top support 1. Unlike prior art where an x-ray cassette may be positioned only in specific locations, the design of this invention enables maximum flexibility of positioning for effective x-ray diagnosis. The placement of the spacers at the periphery maximizes the available open space, while the use of blocks as spacers provides sufficient support for the patient during examination and/or treatment. The transparency of the entire top support provides maximum sight for simple, precise placement of the cassette. The base may be marked with lines (not shown) for easier alignment of the x-ray cassette, if desired.

One side of the top support 1 is hinged to at least one, and preferably more than one, of the side spacers 3 residing on the same side of the base 2, using hinges 6 coupled to the side spacers 3 and the top support 1. The use of rectangular blocks extending along the side of the trauma board is advantageous for effective hinging of the top support 1 to the side spacers. FIG. 2 shows the top support 1 hinged to the side spacers 3 along one side of the trauma board. The opposite side of the top support is then able to rotate toward and away from the base 2, for raising and lowering of the top support 1, which is useful for purposes such as cleaning. The top support 1 remains coupled to the rest of the trauma board, however, and lateral sliding of the top support 1 over the spacers 3, 4, 5 is minimized or eliminated, unlike some of the prior art. In addition, the top support 1 is prevented from undesirably disengaging completely from the rest of the trauma board. To prevent the top support 1 from unexpectedly raising or lowering, the side of the top support opposite from the hinged side may be secured to the side spacers 3 along that side with latching means (not shown).

In one embodiment of the invention, the head end of both the top surface 1 and the base 2 is indented at both opposing sides, as shown in FIG. 1. Preferably, this indention will be about three inches from each side. This indented head end is advantageous both for closer examination of the head of a patient and for precise placement of x-ray cassettes when diagnosing head injuries. Grooves (not shown) may be placed along either side of the indented head end for placement of the cassette.

The foregoing description of a preferred embodiment of the invention has been presented for purposes of illustration and description, and is not intended to be exhaustive or to limit the invention to the precise form disclosed. The description was selected to best explain the principles of the invention and practical application of these principals to enable others skilled in the art to best utilize the invention in various embodiments and various modifications as are suited to the particular use contemplated. It is intended that the scope of the invention not be limited by the specification, but be defined by the claims set forth below.

We claim:

1. An apparatus for supporting a patient during examination, including x-ray examination, comprising:
   a) a rigid base, the base having a top surface, a bottom surface, opposed sides and opposed ends;
   b) a plurality of spacers mounted to and extending along each of the opposed sides of the top surface of the base, leaving an open area between the opposed sides for positioning of an x-ray cassette onto the top surface of the base, the plurality of spacers being separated from one another along each side of the base so as to create at least one opening along each side for insertion of the x-ray cassette; and
   c) a flat, rigid, radiolucent, substantially transparent top support for supporting the patient, the top support having opposed sides and opposed ends, one side of the top support being rotatably hinged to at least two of the spacers so as to allow the side of the top support opposite from the side rotatably hinged to rotate away from and toward the base, thus raising and lowering the top support.

2. The apparatus of claim 1, further comprising additional spacers mounted to and extending fully along each end of the base.

3. The apparatus of claim 1, wherein each of the plurality of spacers has a rectangular cross-section.

4. The apparatus of claim 1, further comprising means for securing the second side of the top support to the plurality of spacers mounted to the second side of the base, the means for securing being configured to secure the top support and prevent the top support from unexpectedly raising.

5. The apparatus of claim 1, wherein one end of the top support and base is indented along both sides, the indentations being about 3 inches from each side.

6. The apparatus of claim 3, wherein the top support is made of acrylic plastic.

7. An apparatus for supporting a patient during examination, including x-ray examination, comprising:
   a) a radiolucent, substantially transparent top support for supporting a patient,
   b) a flat, rigid base;
   c) a plurality of means for vertically spacing the top support and base, each of the plurality of means for vertically spacing being mounted along the periphery of the base, the plurality of means for vertically spacing being separated from one another along each side of the base so as to create means for insertion and positioning of an x-ray cassette; and
   d) means for hinging one side of the top support to the plurality of means for vertically spacing on the same side for raising and lowering the top support.

8. The apparatus of claim 7, further comprising additional spacing means mounted to and extending fully along each end of the base.

9. The apparatus of claim 7, wherein each of the plurality of spacing means has a rectangular cross-section.

10. The apparatus of claim 7, further comprising means for securing the second side of the top support to the plurality of spacers mounted to the second side of the base, the means for securing being configured to secure the top support and prevent the top support from unexpectedly raising.

11. The apparatus of claim 7, wherein one end of the top support and base is indented along both sides, the indentations being about 3 inches from each side.

12. The apparatus of claim 7, wherein the top support is made of acrylic plastic.

13. An apparatus for supporting a patient during examination, including x-ray examination, comprising:
   a) a flat, rigid base having a top surface, first and second opposed sides, a head end, and a foot end;
   b) a flat, rigid top support for supporting a patient, the top support being constructed of a radiolucent, substantially transparent material, the top support having a top surface, a bottom surface, first and second opposed sides, a head end, and a foot end;
   c) a plurality of spacers mounted to the top surface of the base axially along the periphery of the first side of the base to vertically separate the base and the top support, the plurality of spacers being separated so as to create openings along the periphery of the first side for the insertion of an x-ray cassette;
   d) a plurality of spacers mounted to the top surface of the base axially along the periphery of the second side of the base to vertically separate the base and the top support, the plurality of spacers along the second side being separated so as to create openings along the periphery of the second side for the insertion of the x-ray cassette,
   the spacers, top surface and base creating an open space for positioning of the x-ray cassette, the open space having a width extending from the plurality of spacers on the first end and the spacers on the second end, a length extending from the head end of the base and top support to the foot end of the base and top support, and a height extending from the top surface of the base to the bottom surface of the top support; and
   e) a plurality of hinges coupling the first side of the top support to at least one of the plurality of spacers mounted to the first side of the base so as to allow the second side of the top support to rotate away from and toward the base, thereby raising and closing the top support.

14. The apparatus of claim 13, further comprising additional spacers mounted to and extending fully along each end of the base.

15. The apparatus of claim 13, wherein each of the plurality of spacers has a rectangular cross-section.

16. The apparatus of claim 13, further comprising means for securing the second side of the top support to the plurality of spacers mounted to the second side of the base, the means for securing being configured to secure the top support and prevent the top support from unexpectedly raising.

17. The apparatus of claim 13, wherein one end of the top support and base is indented along both sides, the indentations being about 3 inches from each side.

18. The apparatus of claim 13, wherein the top support is made of acrylic plastic.

19. An apparatus for supporting a patient during examination, including x-ray examination, comprising:
   a) a flat, rigid base having a top surface, first and second opposed sides, a head end and a foot end;
   b) a flat, rigid top support constructed of radiolucent, substantially transparent material, the top support having first and second sides, a head end and foot end, and a top and bottom surface; and
   c) a plurality of spacers mounted to the periphery of the top surface of each of the first and second sides of the base, the plurality of spacers mounted to the first side of the base being hinged to the first side of the top support for raising and lowering of the top support, the plurality of spacers being spaced apart along the first and second sides of the base so as to permit the insertion of an x-ray cassette, wherein the width between the plurality of spacers on the first and second sides of the base, the height between the top surface of the base and the bottom surface of the top support, and the length between the head end and foot end of the base and top support define a volume of open space for positioning of the x-ray cartridge.

\* \* \* \* \*